United States Patent [19]
Ito et al.

[11] Patent Number: 6,142,930
[45] Date of Patent: Nov. 7, 2000

[54] ELECTRONIC ENDOSCOPE HAVING COMPACT CONSTRUCTION

[75] Inventors: Keiji Ito; Hiroyuki Katsurada; Hirohisa Ueda, all of Tokyo, Japan

[73] Assignee: Asahi Kogaku Kogyo Kabushiki Kaisha, Tokyo, Japan

[21] Appl. No.: 09/005,752

[22] Filed: Jan. 12, 1998

[30] Foreign Application Priority Data

| Jan. 13, 1997 | [JP] | Japan | 9-003435 |
| Jan. 13, 1997 | [JP] | Japan | 9-003437 |
| Jan. 13, 1997 | [JP] | Japan | 9-003439 |
| Jan. 28, 1997 | [JP] | Japan | 9-013737 |
| Jan. 29, 1997 | [JP] | Japan | 9-014993 |

[51] Int. Cl.$^7$ ........................................................ A61B 1/05
[52] U.S. Cl. ........................... 600/109; 600/110; 600/129; 348/76
[58] Field of Search .................................. 600/109, 110; 348/65, 76, 294; 358/483, 482

[56] References Cited

U.S. PATENT DOCUMENTS

| 4,890,159 | 12/1989 | Ogiu | 600/109 |
| 4,895,138 | 1/1990 | Yabe . | |
| 4,905,082 | 2/1990 | Nishigaki et al. . | |
| 5,021,888 | 6/1991 | Kondou et al. . | |
| 5,220,198 | 6/1993 | Tsuji . | |
| 5,325,847 | 7/1994 | Matsuno . | |
| 5,411,020 | 5/1995 | Ito . | |
| 5,427,087 | 6/1995 | Ito . | |
| 5,754,313 | 5/1998 | Pelchy et al. | 348/65 |
| 5,857,963 | 1/1999 | Pelchy et al. | 600/109 |

FOREIGN PATENT DOCUMENTS

| 0745347 | 12/1996 | European Pat. Off. . |
| 5-261065 | 10/1963 | Japan . |
| 5-88546 | 11/1988 | Japan . |
| 1113215 | 7/1989 | Japan . |
| 3-2813 | 1/1991 | Japan . |
| 4313717 | 11/1992 | Japan . |
| 4317280 | 11/1992 | Japan . |
| 5115435 | 5/1993 | Japan . |
| 5115436 | 5/1993 | Japan . |
| 5-261065 | 10/1993 | Japan . |
| 8148666 | 6/1996 | Japan . |
| 8201706 | 8/1996 | Japan . |
| 8271809 | 10/1996 | Japan . |
| 2322499 | 8/1998 | United Kingdom . |

OTHER PUBLICATIONS

A Search Report issued by the Patent Office on Apr. 9, 1998 in counterpart U.K. Patent Application GB 9800698.4.

Copy of the Patent Abstracts of Japan, Section C, Section No. 1153, vol. 18, No. 30, p. 131, dated Jan. 17, 1994.

Primary Examiner—John P. Leubecker
Attorney, Agent, or Firm—Greenblum & Bernstein, P.L.C.

[57] ABSTRACT

An electronic endoscope with which the electrical insulation between side faces of a solid-state imaging element and inner leads of a flexible circuit board will be secured and with which the external dimension after assembly of the unit comprised of the solid-state imaging element and the flexible circuit board can be made small. The inner leads of the flexible circuit board are bonded to pad parts disposed on the solid-state imaging element, and these inner leads are bent so as to be disposed along the side faces of the solid-state imaging element. An electrically insulating tape is attached to the side faces of the solid-state imaging element along which inner leads are disposed.

25 Claims, 16 Drawing Sheets

ELECTRONIC ENDOSCOPE HAVING COMPACT CONSTRUCTION

BACKGROUND OF THE INVENTION

The present invention relates to a structure for an electronic endoscope, and in particular to a structure to be installed in a front end part of an electronic endoscope which is inserted into a body cavity for endoscopic observation and which is provided with a solid-state imaging element for capturing endoscopic images.

(1) In order to improve insertion ability of an endoscope, i.e. to reduce pain to a patient during endoscopic observation, smaller the size of a front end part of the endoscope is better. An electronic endoscope needs to equip, in its front end part, with a solid-state imaging element for capturing endoscopic images obtained by an objective lens group as well as arrangements for electrically connecting the solid-state imaging element to a wiring circuit board and for providing necessary electric insulation, and thus the front end part of the electronic endoscope tends to become bulky. Accordingly, an object of the present invention is to provide a structure for a front end part of an electronic endoscope, which can reduce the size of the front end part of the electronic endoscope to thereby improve the insertion ability thereof.

(2) In order to avoid unwanted marginal rays from reaching a rectangular light receiving surface of a solid-state imaging element and thus to improve obtained endoscopic images, Japanese laid-open patent publication No. Hei-3-2813 proposes providing a rectangular shading mask for blocking the unwanted marginal rays inside the objective optical group or on the surface of the first foremost lens.

However, when a shading mask is disposed inside the objective optical group, not only does the assembly of the objective optical group become troublesome, but since the unwanted marginal rays can still enter up to the position of the shading mask inside the objective optical group, flare, etc., may occur due to the reflection or the like before marginal rays reach the shading mask.

In case where the shading mask is disposed on the surface of the first lens, the shading mask protrudes from the surface of the first foremost lens, making it difficult to remove foul fluids, etc., that have become attached to the surface of the first foremost lens and thus leading to significant degradation of the picture quality of the observed image.

Accordingly, another object of the present invention is to provide a structure for a front end part of an electronic endoscope, which can positively avoid entry of unwanted marginal rays into an objective optical group or system without the use of a shading mask so that satisfactory picture quality without flare, etc., can be obtained.

In an endoscope, a first lens (a foremost lens such as a cover glass, a convex lens) of a lens group is generally fitted onto an observation window, which is the entrance window through which the optical image enters the objective lens group.

The observation window is generally provided at a front end part of the endoscope. During assembly, a lens frame in which objective lens or lenses other than the first lens is installed is assembled to the rear portion of the front end part on which the first lens has already been mounted.

Therefore, dust or debris is like to be attached to the rear face of the first lens before the lens frame is installed at the prescribed position inside the front end part, and the work of removing such debris from the rear side of the front end part is extremely difficult.

Accordingly, another object of the present invention is to provide a structure for a front end part of electronic endoscope, which can be assembled readily and which can eliminate the problem of dropping of debris onto the rear face of the first optical member during the process of installing the objective optical group into the front end part of the endoscope.

SUMMARY OF THE INVENTION

To attain the object, the present invention provides a structure for an electronic endoscope, comprising:
  a solid-state imaging element including:
    a light receiving surface;
    pad parts on a portion adjacent the light receiving surface;
    a side face defining an edge at junction between the portion and the side face;
  a flexible circuit board having inner leads connected to the pad parts, the inner leads being bent to extend along the side face in a rearward direction; and
  an electrically insulating material provided between the side face and the inner leads, the insulating material being elongated from the edge along the side face in the rearward direction.

The electrically insulating material can be formed by an electrically insulating tape attached to the side face, a plurality of electrically insulating tape attached to areas of the side face where the inner leads lie, a reinforcing plate attached to the inner leads, coating applied to the inner leads, a sheet laminated on the inner leads, or the like.

Preferably, the electrically insulating material has a thickness of 0.01 mm to 0.1 mm.

The present invention further provides a structure for an electronic endoscope, comprising:
  a lens group; and
  a solid-state imaging element including a rectangular light receiving surface, the rectangular light receiving surface being disposed at a position at which subject image is formed by the lens group,
  wherein a first optical member of the lens group has a rectangular shape that is analogous (similar in figure) to a shape of the rectangular light receiving surface and that has a size prohibit unwanted marginal light rays from entering into the lens group.

In the structure, it is preferable that all lenses of the lens group and the solid-state imaging element are assembled as a single unit detachably mounted to a front end of the endoscope.

The present disclosure relates to the subject matters contained in Japanese patent application Nos. 9-3435, 9-3437 and 9-3439 (all filed on Jan. 13, 1997), 9-13737 (filed on Jan. 28, 1997) and 9-14993 (filed on Jan. 29, 1997), which are expressly incorporated herein by reference in their entirety.

DETAILED DESCRIPTION OF ELECTRONIC ENDOSCOPE

Figure 2:
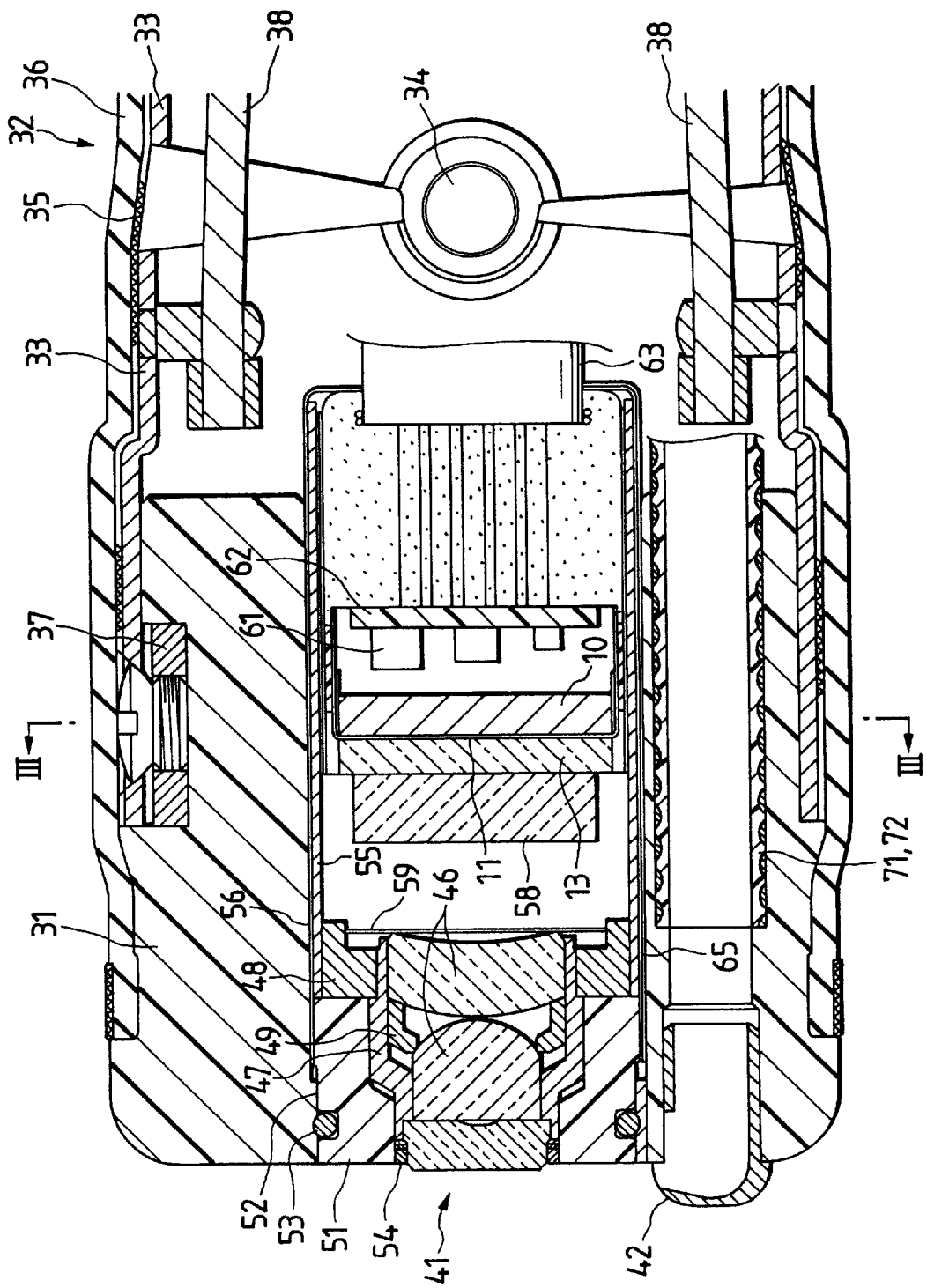
FIG. 2 is a cross-sectional side view of a front end of an inserted part of an endoscope in which the unit shown in FIG. 1 has been installed.
Figure 3:
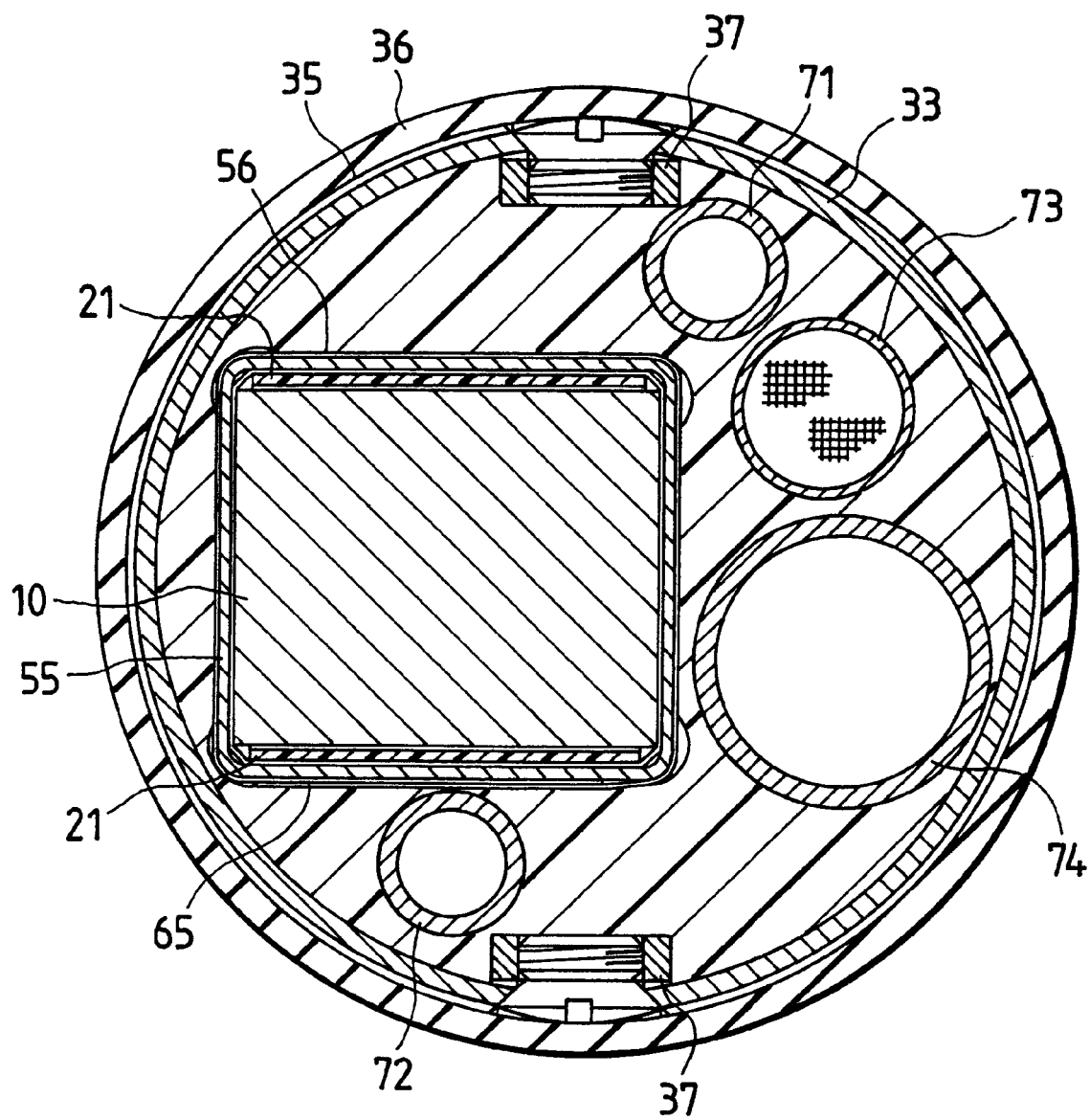
FIG. 3 is a cross section taken along line III—III in FIG. 2.

FIG. 2 shows a front end portion of an inserted part of an endoscope and FIG. 3 shows the cross section along line III—III of FIG. 2.

A front end body 31 is formed as a single part from an electrically insulating plastic material, such as modified polyphenylene oxide, polysulfone, etc., and is connected to a front end portion of a bendable part 32. The bendable part 32 is disposed at a front end of a thin flexible inserted part, and remote-controlled to be bent as desired.

The bendable part 32 includes connecting a plurality of joint rings 33 rotatably connected to one another by means of rivets 34, a net tube covering the outer periphery of joint rings 33, and a jacket 36, made from a rubber tube, etc., covering the outer surface of the net tube 35. The front end part of the jacket 36 is tightly bound and joined to the outer peripheral surface of front end body 31. Reference numeral 38 is a manipulating wire for controlling degree of bend.

The front end body 31 and the bendable part 32 are connected together such that the forefront joint ring 33 is screwed to a pair of metal threaded pieces 37 (only one metal threaded piece 37 is shown in FIG. 2), each having a female thread and being embedded in a dented part of the front end body 31.

The endoscope is a so-called front view type endoscope arranged for observation in the forward direction, and an observation window 41 and an air/water delivery nozzle 42 are provided along with an unillustrated illumination window, forceps channel exit hole, etc. on the front end face of the front end body 31. Reference numerals 71 and 72 are the front end portions of the air delivery and water delivery tubes, 73 in FIG. 3 is an illumination light guide fiber bundle, and 74 is a forceps channel.

Provided inwardly of the observation window 41 is an objective lens group 46 which is fixed inside a metal lens frame 47 with a prescribed interval being set between the lenses by means of a spacer 49. An insulating ring 51, made of electrically insulating plastic material, is adhered onto the outer peripheral portion of the front half of lens frame 47.

The outer peripheral surface of the insulating ring 51 is fitted into a hole 52 of the circular cross section that is formed parallel to the axial direction at the front end portion of the front end body 31, and an O-ring 53 for seal is fitted to the fitting part. Reference numeral 54 is a defoamed, electrically insulating adhesive agent.

A connecting member 48, with a rectangular external shape, is fixed to the rear end portion of the lens frame 47, and the front end portion of a metal shield pipe 55 is fitted and joined to the outer peripheral part of this connecting member 48.

A shield pipe 55 is fitted inside a rectangular hole 56, that is made continuous with the circular hole 52 and passes through to the rear end of the front end body 31. A solid-state imaging element 10, which for example is comprised of a charge coupled device (CCD), is fixed inside the shield pipe 55 so that the light receiving surface 11 is directed forwardly.

A color compensation filter 58 is adhered onto the front face of a cover glass 13 which in turn is provided on the front face of light receiving surface 11. Reference numeral 59 is a shading mask for blocking the unwanted light around the periphery of the light path.

Figure 4:
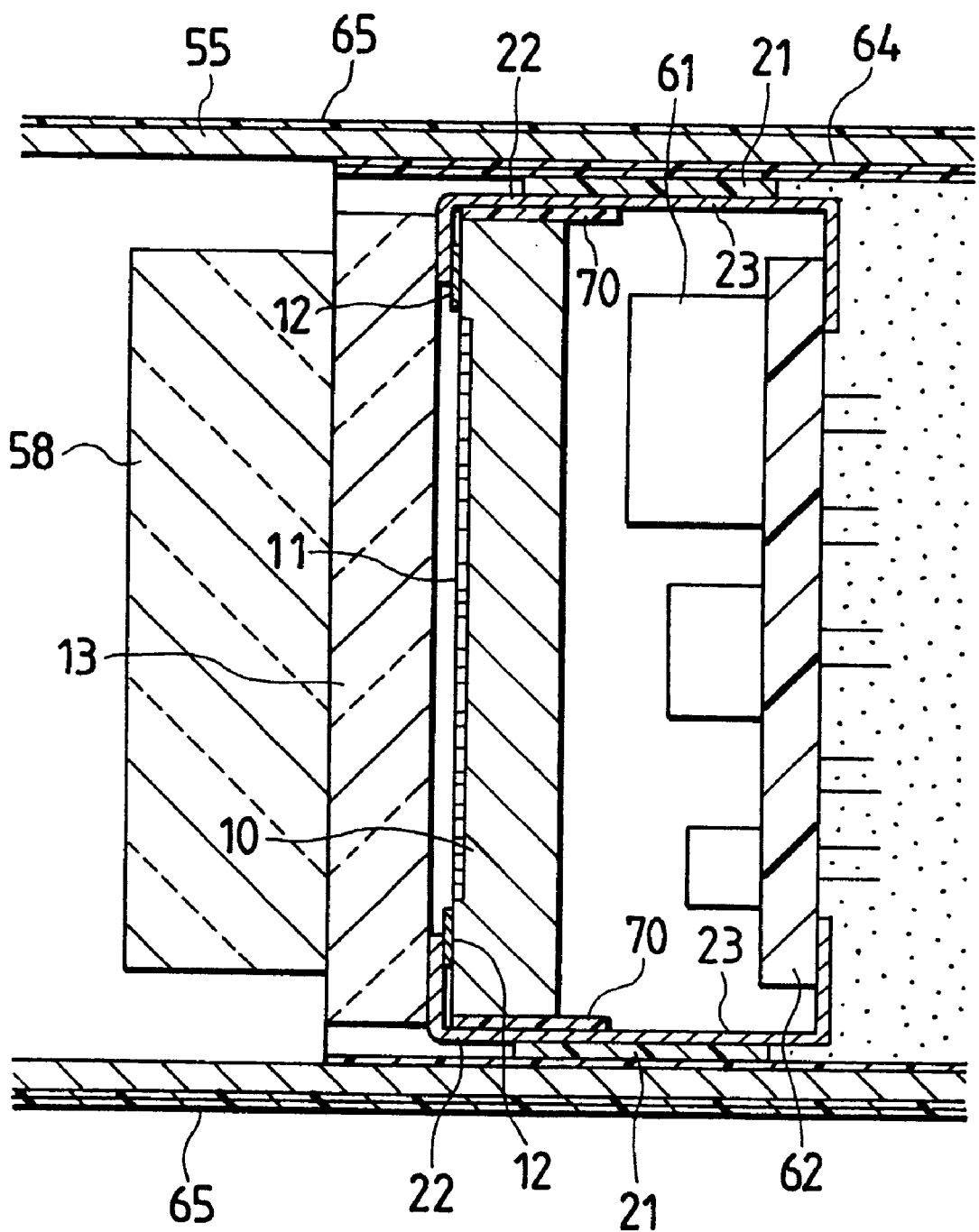
FIG. 4 is an enlarged, cross-sectional partial side view of the surroundings of the unit inside the front end of the inserted part of the endoscope.

As shown in enlarged manner in FIG. 4, electronic parts 61 for processing the signals input to and output from the solid-state imaging element 10 are mounted on a wiring circuit board 62 and disposed behind the solid-state imaging element 10 inside the shield pipe 55. A signal cable 63 is drawn rearwardly from the electronic parts 61.

Insulating tapes 64 and 65 are respectively wound around the outer peripheral surfaces of the parts disposed inside the shield pipe 55 and the outer peripheral surface of the shield pipe 55 to electrically insulate the shield pipe 55 from the inside and outside parts.

A TAB (tape automating bonding) type flexible circuit board 20 is attached to the solid-state imaging element 10, and leads 23 of this flexible circuit board 20 are bent inwards at their rear end portions for connection to the wiring circuit board 62.

Figure 5:
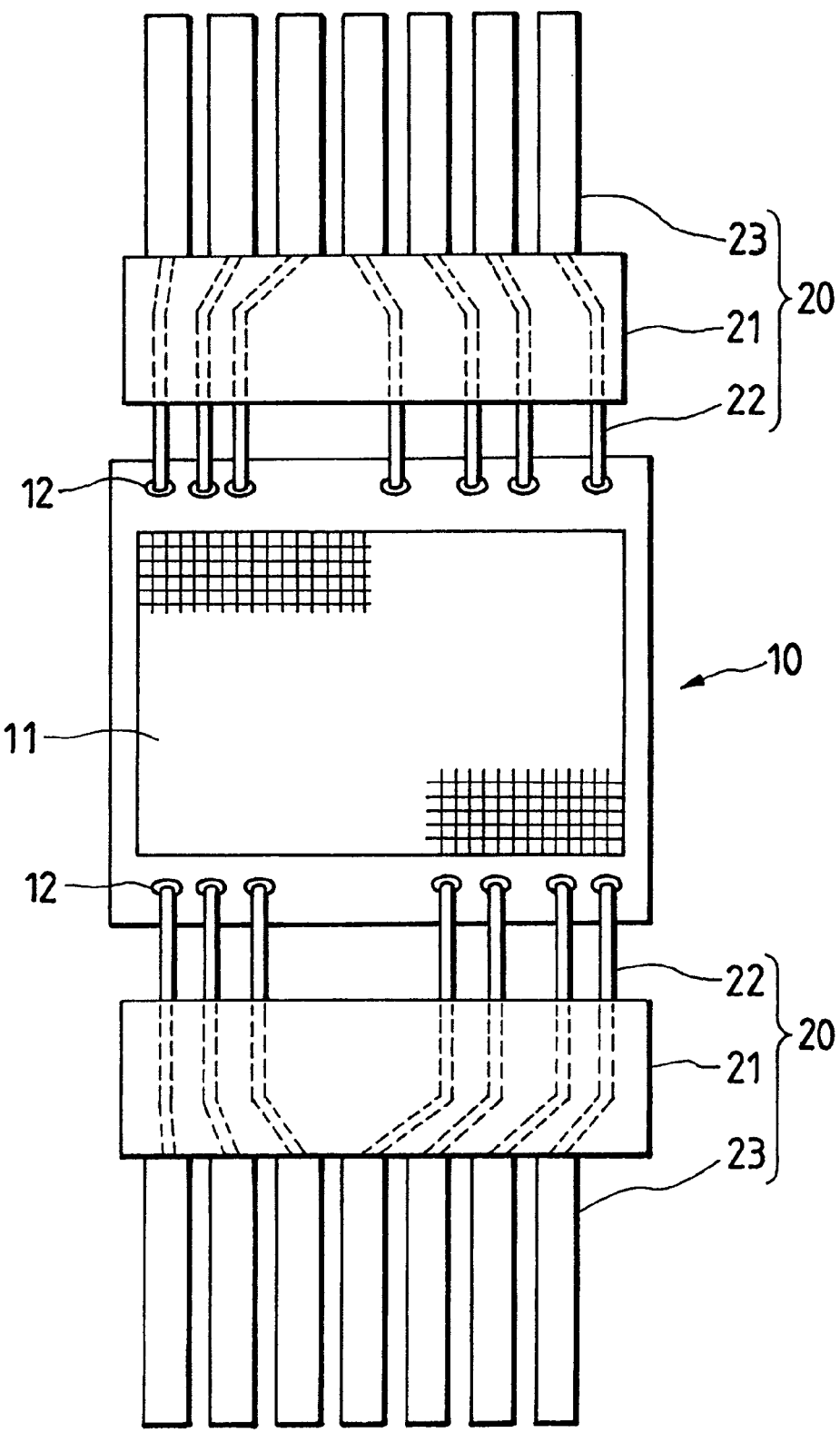
FIG. 5 is a front view of a condition of the unit before the inner leads are bent.

Prior to being installed inside the shield pipe 55, the solid-state element 10 and the flexible circuit board 20 are connected together, as shown in FIG. 5, by the bonding of the tips of inner leads 22 of the flexible circuit board 20 to pad parts 12 disposed at both sides of and on the same surface as the light receiving surface 11 of the solid-state imaging element 10. A cover glass 13 is then coupled so as to cover the light receiving surface 11 and the bonded parts.

Reference numeral 21 is a reinforcing plate for the flexible circuit board 20 and is formed from a thin, electrically insulating plate, for example, of polyimide resin. The leads 23 for connection with the wiring circuit board 62 are disposed so as to extend outwardly from the reinforcing plate 21 as shown in FIG. 5. The inner leads 22 and leads 23 are both formed from copper material.

When the unit thus constructed by the solid-state imaging element 10 and the flexible circuit board 20 is installed inside the shield pipe 55, the inner leads 22 are bent so as to be disposed along the side face of the solid-state imaging element 10 and directed rearwardly from the surface where the light receiving surface 11 is provided.

Figure 1:
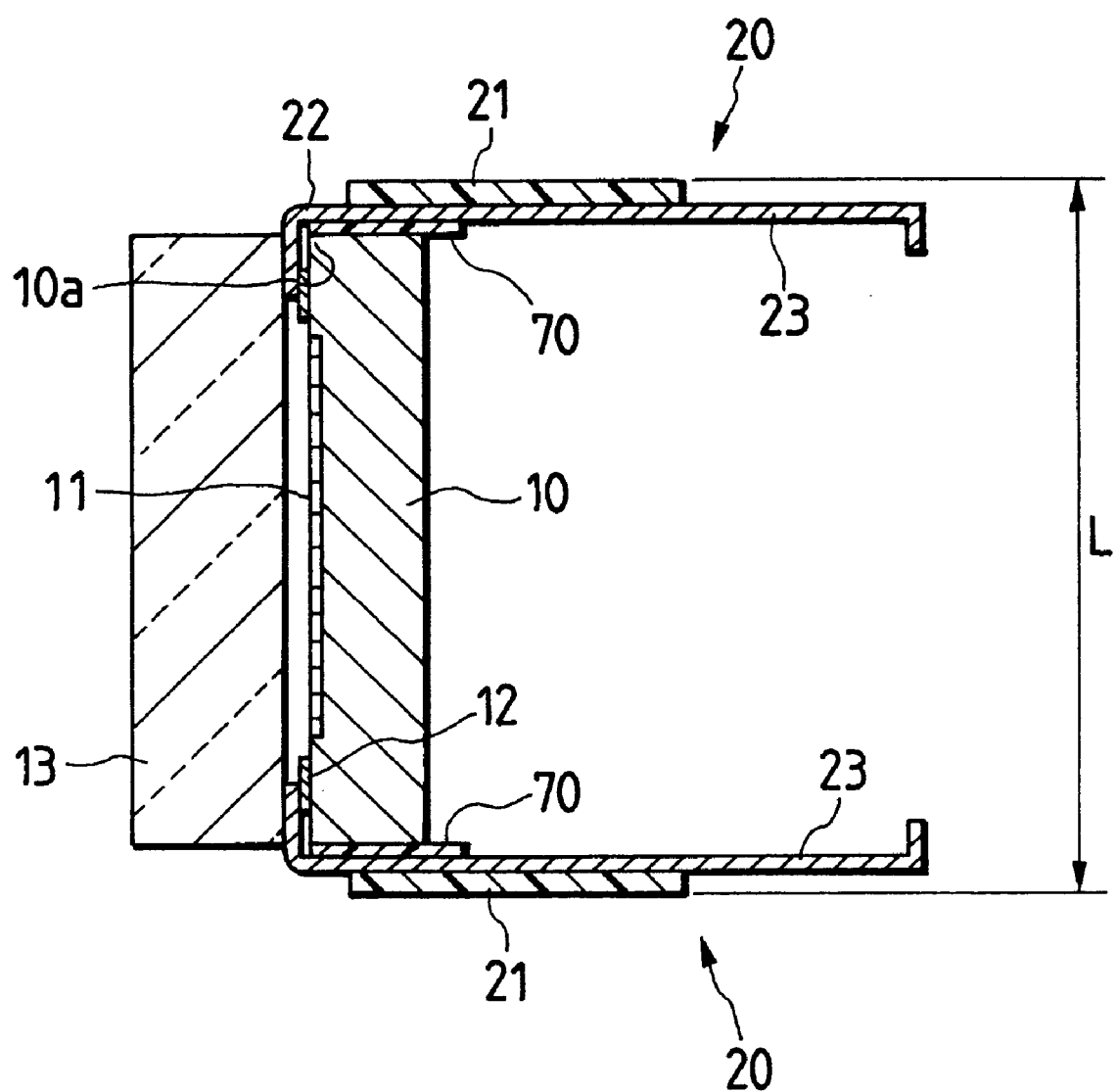
FIG. 1 is a cross-sectional side view of a condition of an unit comprised of a solid-state imaging element and a flexible circuit board after inner leads have been bent.

FIG. 1 shows the condition in which the inner leads 22 are bent in the above manner. A thin, electrically insulating tape (or tapes) 70, made for example from polyester or polyimide, etc., is attached to the side face of solid-state imaging element 10 where the inner leads 22 are disposed in order to provide electric insulation between the side face of the solid-state imaging element 10 and the inner leads 22.

The front end part of this insulating tape 70 is positioned at the same position as the front end of the solid-state imaging element 10 while the rear end part of the insulating tape 70 is disposed so as to extend rearwardly from the rear end of the solid-state imaging element 10. The electrical insulation between the side face of the solid-state imaging element 10 and the inner leads 22 is thereby secured. In particular, since the front end part of this insulating tape 70 is positioned at the same position as the front end of the solid-state imaging element 10, the electrical insulation between the edge 10a of the solid-state imaging element 10 and the inner leads 22 is secured.

The thickness of the insulating tape 70 is within the range of 0.01 mm to 0.1 mm. The external dimension L after assembly of the unit comprised of the solid-state imaging element 10 and the flexible circuit board 20 upon the bending of the inner leads 22 will thus be small as shown in FIG. 1. The diameter of front end body 31 can thus be made small to provide excellent insertion properties that will not inflict much pain to a patient.

Figure 6:
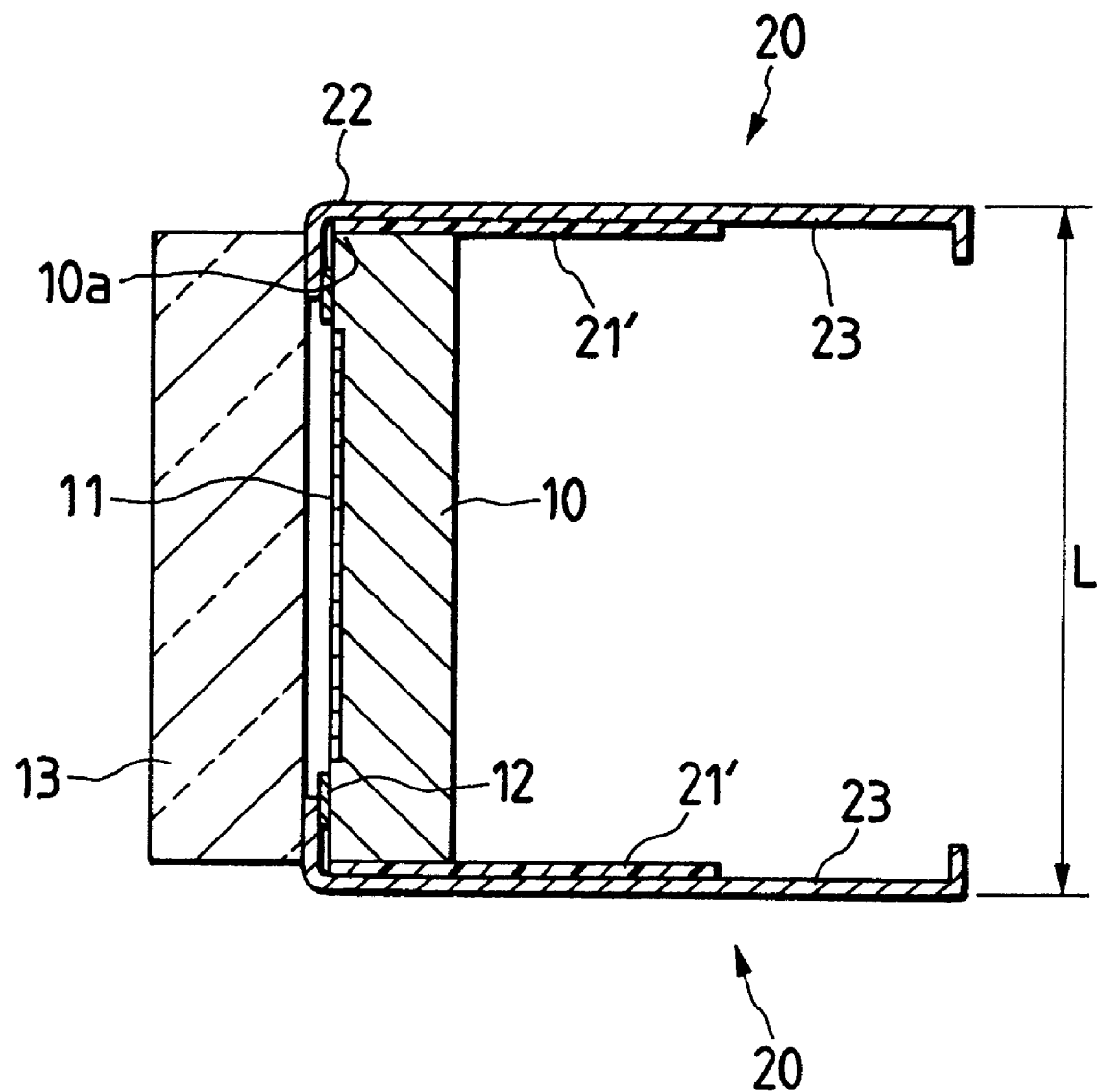
FIG. 6 is a cross-sectional side view of a condition of another unit comprised of a solid-state imaging element and a flexible circuit board after inner leads have been bent.
Figure 7:
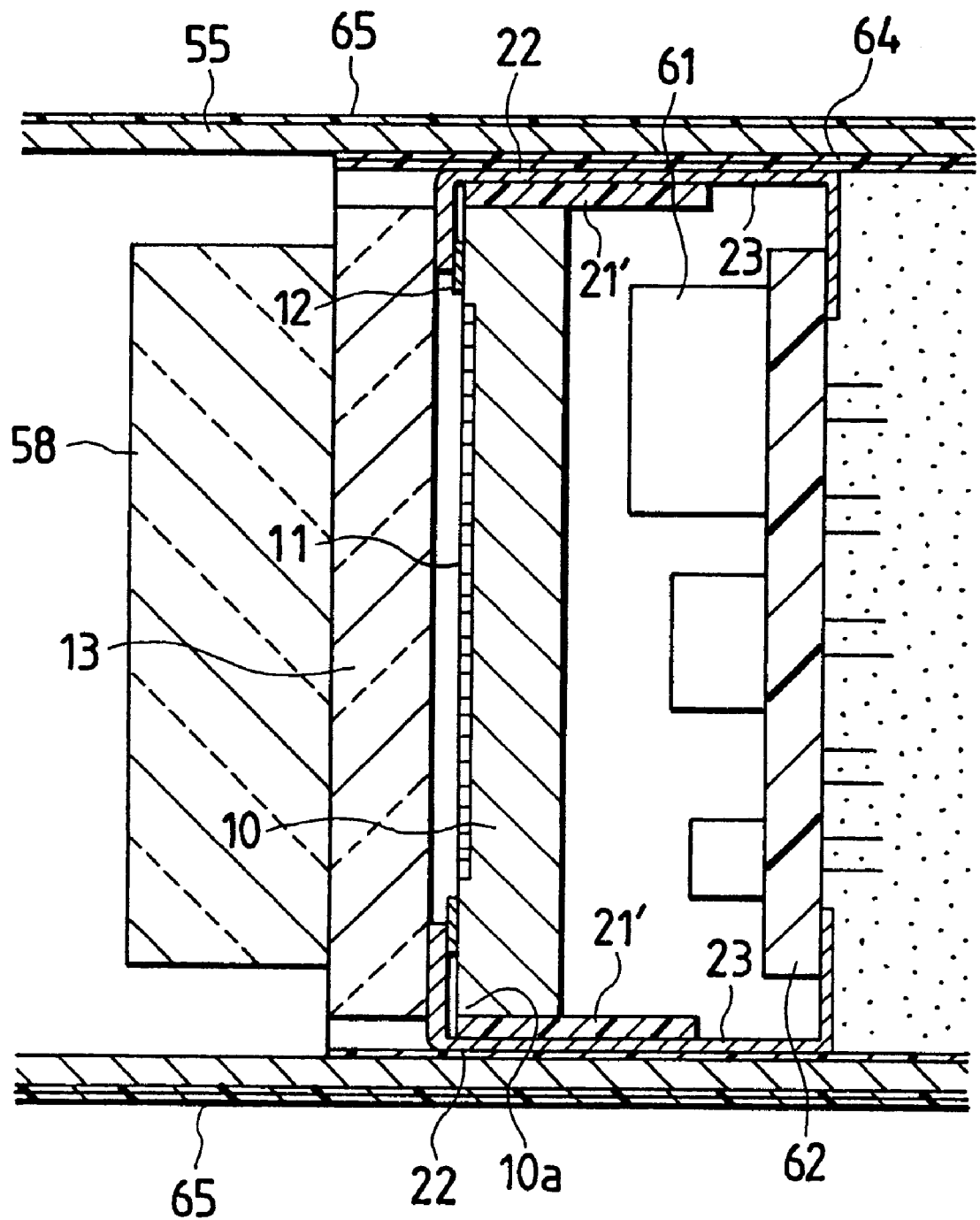
FIG. 7 is a enlarged, cross-sectional partial side view of the surroundings of the unit shown in FIG. 6 inside the front end of the inserted part of the endoscope.
Figure 8:
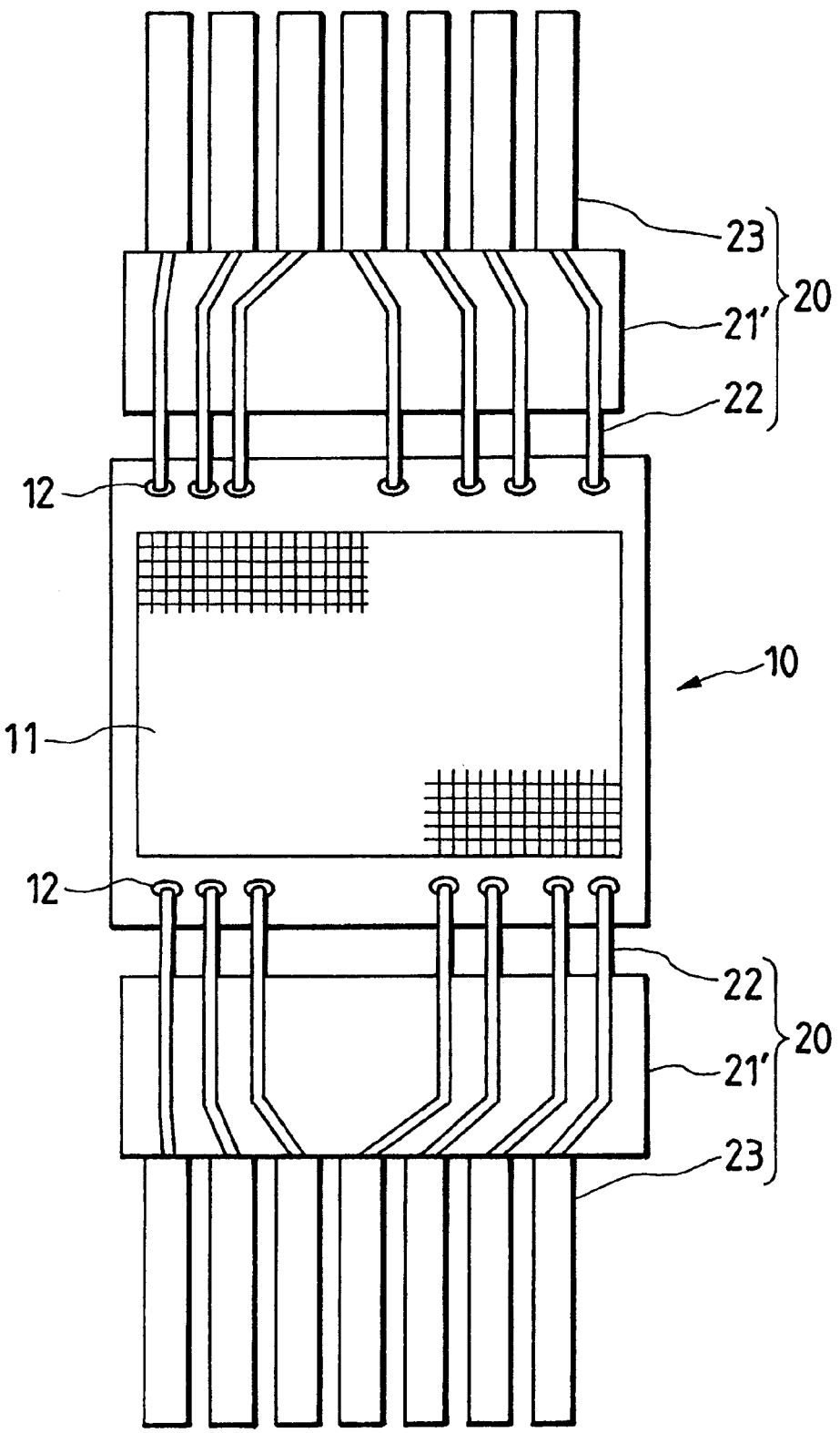
FIG. 8 is a front view of a condition of the unit shown in FIG. 6 before the inner leads are bent.

The reinforcing plate 21 may be provided between the inner leads 22 and the side face of the solid-state imaging element 10, and in this case, the insulating tape 70 can be dispensed with, as indicated by reference numeral 21' in FIGS. 6 to 8.

Reference numeral 21' indicates a reinforcing plate for reinforcing the inner leads 22 on the flexible circuit board 20. The reinforcing plate 21' is formed from a thin electrically insulating plate, for example, of polyimide resin. The reinforcing plate 21' is attached to the inner side of the inner leads 22 such that the front end of the reinforcing plate is located at the same position as the front end of the solid-state imaging element 10 when the inner leads 22 are bent so as to extend rearwardly.

FIG. 6 shows the condition where the inner leads 22 have been bent. Each reinforcing plate 21' is attached to the inner leads 22 so as to be positioned between the side face of the solid-state imaging element 10 and the inner leads 22.

In this condition, the front end part of each reinforcing plate 21' is located at the same position as the front end of the solid-state imaging element 10 and the rear end part of each reinforcing plate 21' is extended rearwardly from the rear end of the solid-state imaging element 10 so that the electric insulation is secured between the side faces of the solid-state imaging element 10 and the inner leads 22 as well as each reinforcing plate 21' sufficiently reinforces the inner leads 22. In particular, since the front end part of this reinforcing plate 21' is positioned at the same position as the front end of the solid-state imaging element 10, the electrical insulation between the edge 10a of the solid-state imaging element 10 and the inner leads 22 is secured.

By the above arrangement, the external dimension L after assembly of the unit comprised of the solid-state imaging element 10 and the flexible circuit board 20 upon bending of the inner leads 22 will be small as shown in FIG. 6. The diameter of the front end body 31 can thus be made small to provide excellent insertion properties that will not inflict much pain to a patient.

Figure 9:
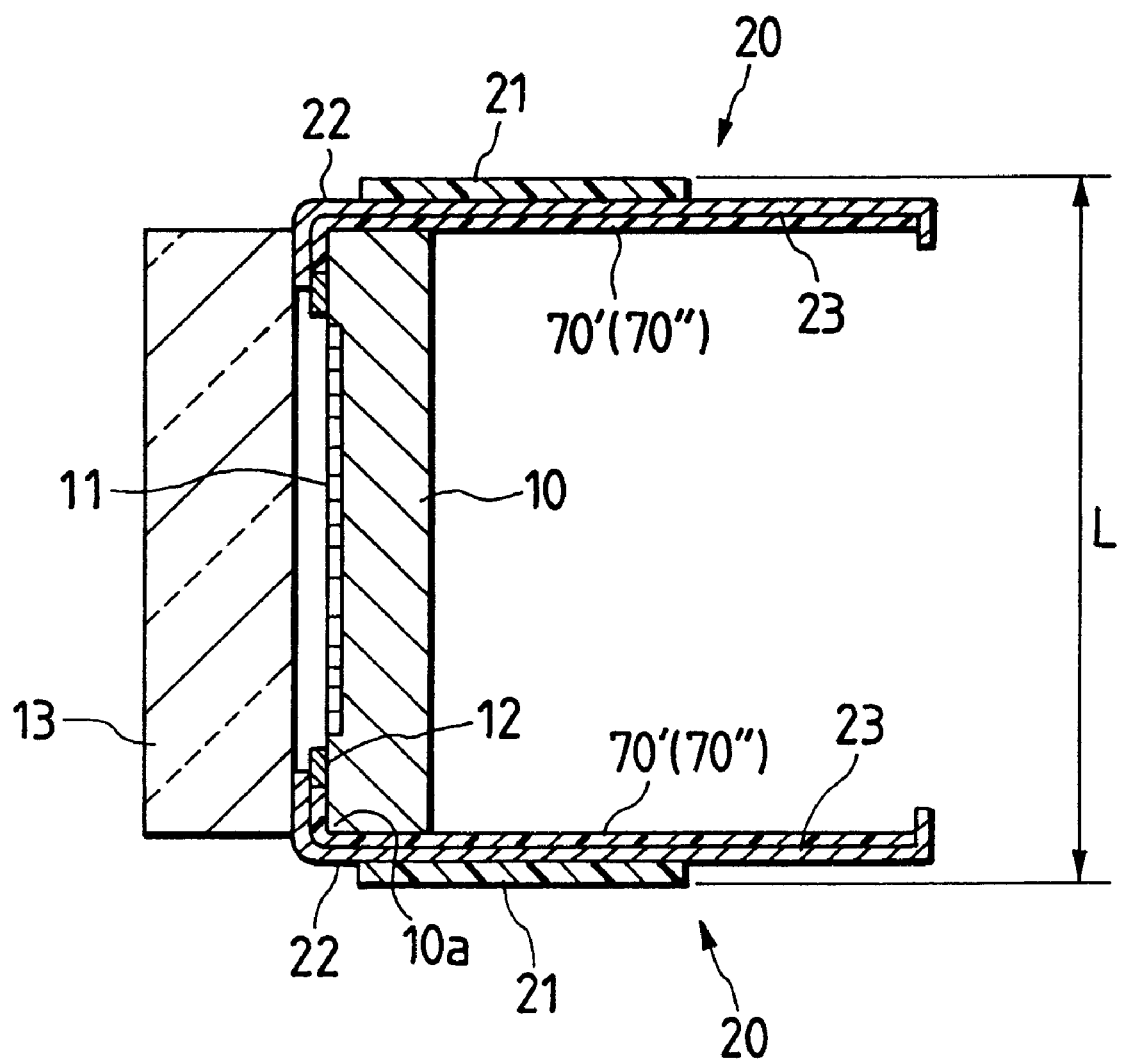
FIG. 9 is a cross-sectional side view of a condition of another unit comprised of a solid-state imaging element and a flexible circuit board after inner leads have been bent.

In the structure shown in FIG. 9, an insulating material or member, such as an insulating tape 70, is provided onto the side face of the solid-state imaging element 10 prior to the bending of the inner leads 22. Such insulating material or member may be provided onto the inner leads 22 not onto the side face of the solid-state imaging element 10 prior to the bending of the inner leads 22 as indicated by reference numerals 70' and 70" in FIGS. 9 to 12.

Figure 10:
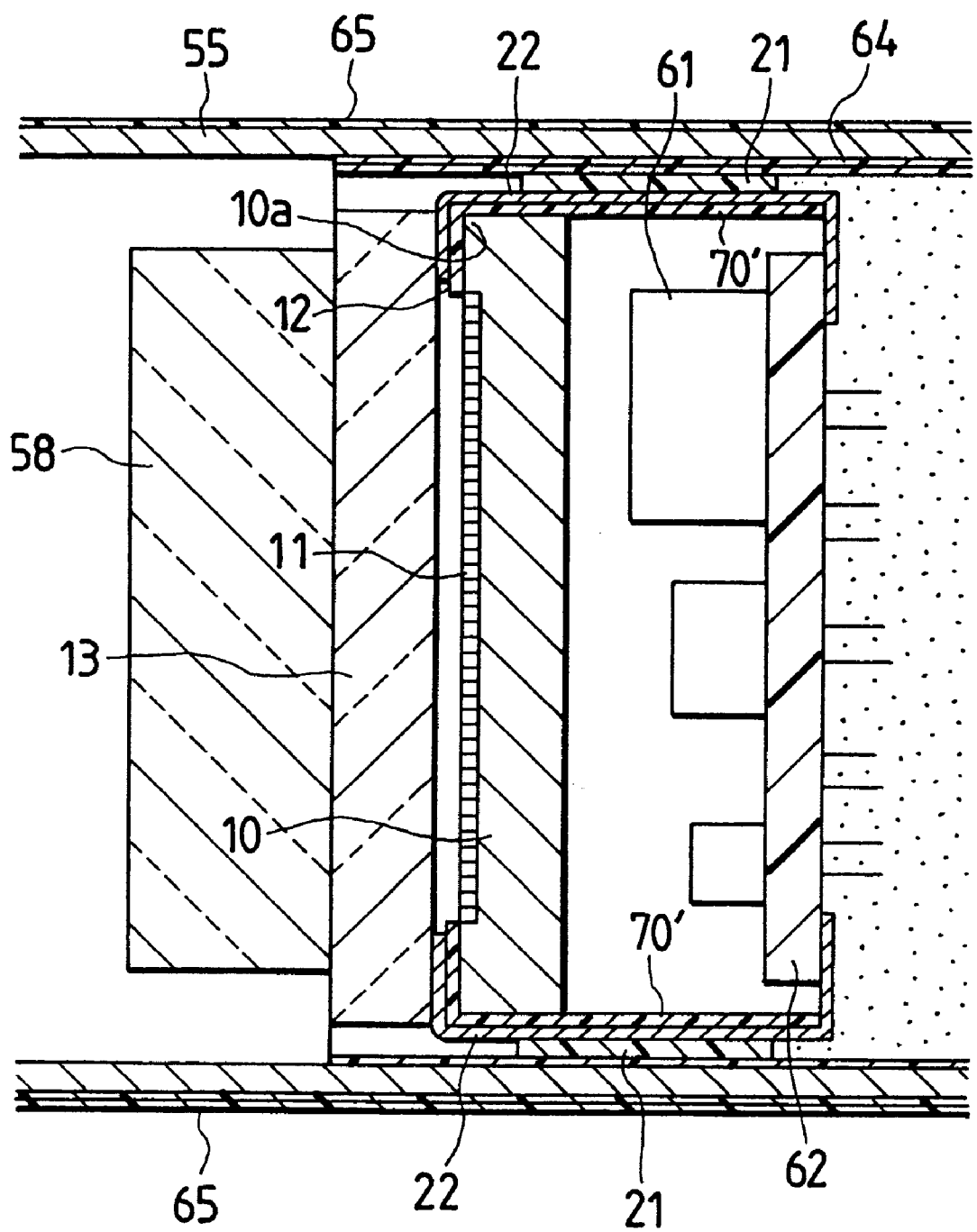
FIG. 10 is an enlarged, cross-sectional partial side view of the surroundings of the unit shown in FIG. 9 inside the front end of the inserted part of the endoscope.
Figure 11:
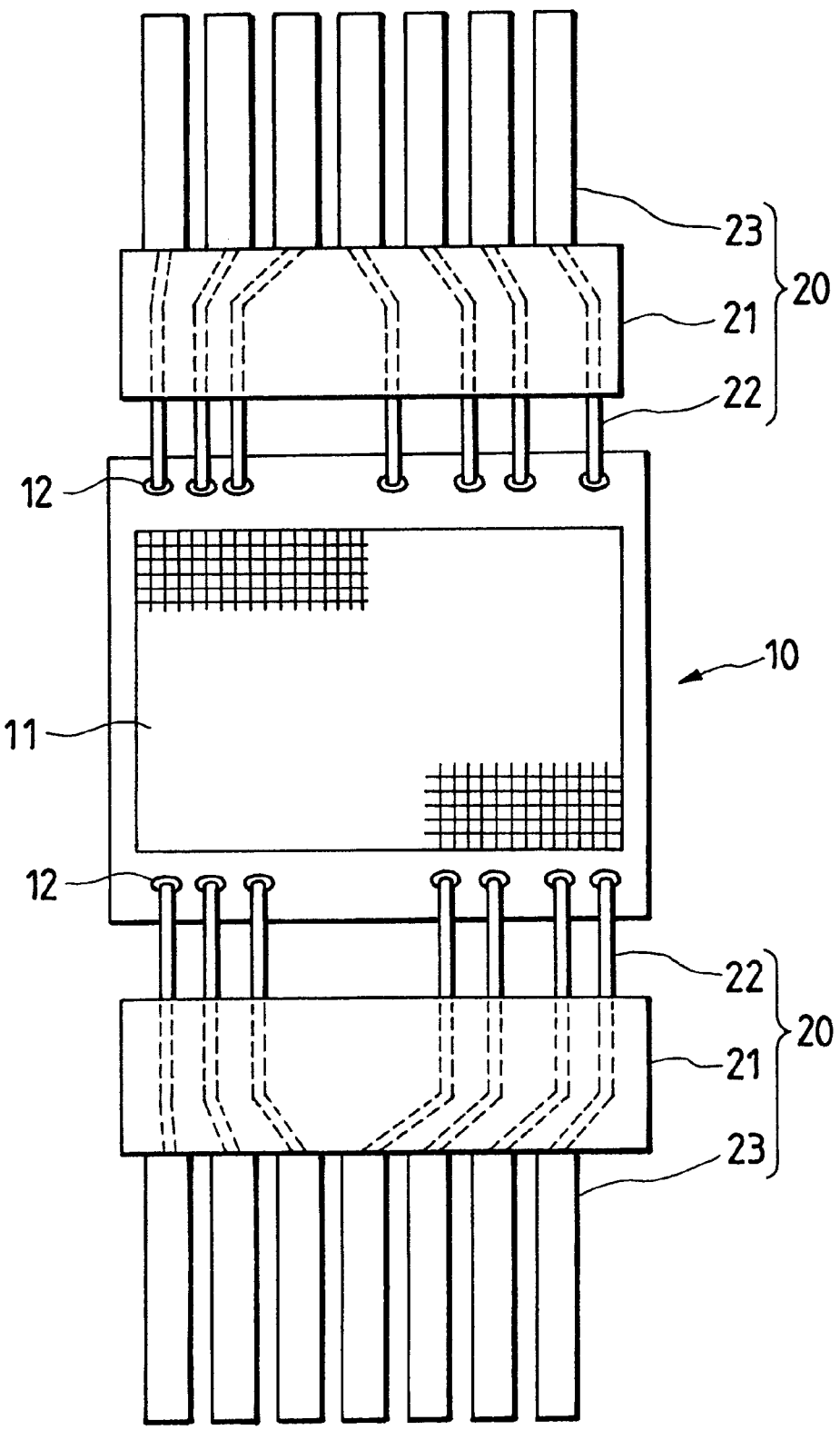
FIG. 11 is a front view of a condition of the unit shown in FIG. 9 before the inner leads are bent.

In the structure shown in FIGS. 9 to 11, the inner leads 22 and the leads 23 are both formed of copper material, etc., and an electrical insulating material 70', such as a silicone adhesive agent, is thinly applied to the rear (or inner) surface of the inner leads 22 and the leads 23 with the exception of bonded portions of the inner leads 22 and end portions of leads 23. The thickness of this electrical insulating material 70' is in the range of 0.01 mm to 0.1 mm.

FIG. 9 shows the condition where the inner leads 22 have been bent. The electrical insulating material 70' applied to the rear surface of the inner leads 22 is sandwiched between the side face of the solid-state imaging element 10 and the inner leads 22 to electrically insulate these members from each other. Since the electrical insulating material 70' is also sandwiched between the front face of the solid-state imaging element 10 and the inner leads 22, the electrical insulation between the edge 10a of the solid-state imaging element 10 and the inner leads 22 is secured positively.

As has been mentioned above, the thickness of electrically insulation 70' is in the range of 0.01 mm to 0.1 mm. The external dimension L after assembly of the unit comprised of the solid-state imaging element 10 and the flexible circuit board 20 upon bending of the inner leads 22 will thus be small as shown in FIG. 9. The diameter of the front end body 31 can thus be made small to provide excellent insertion properties that will not inflict much pain to a patient.

Figure 12:
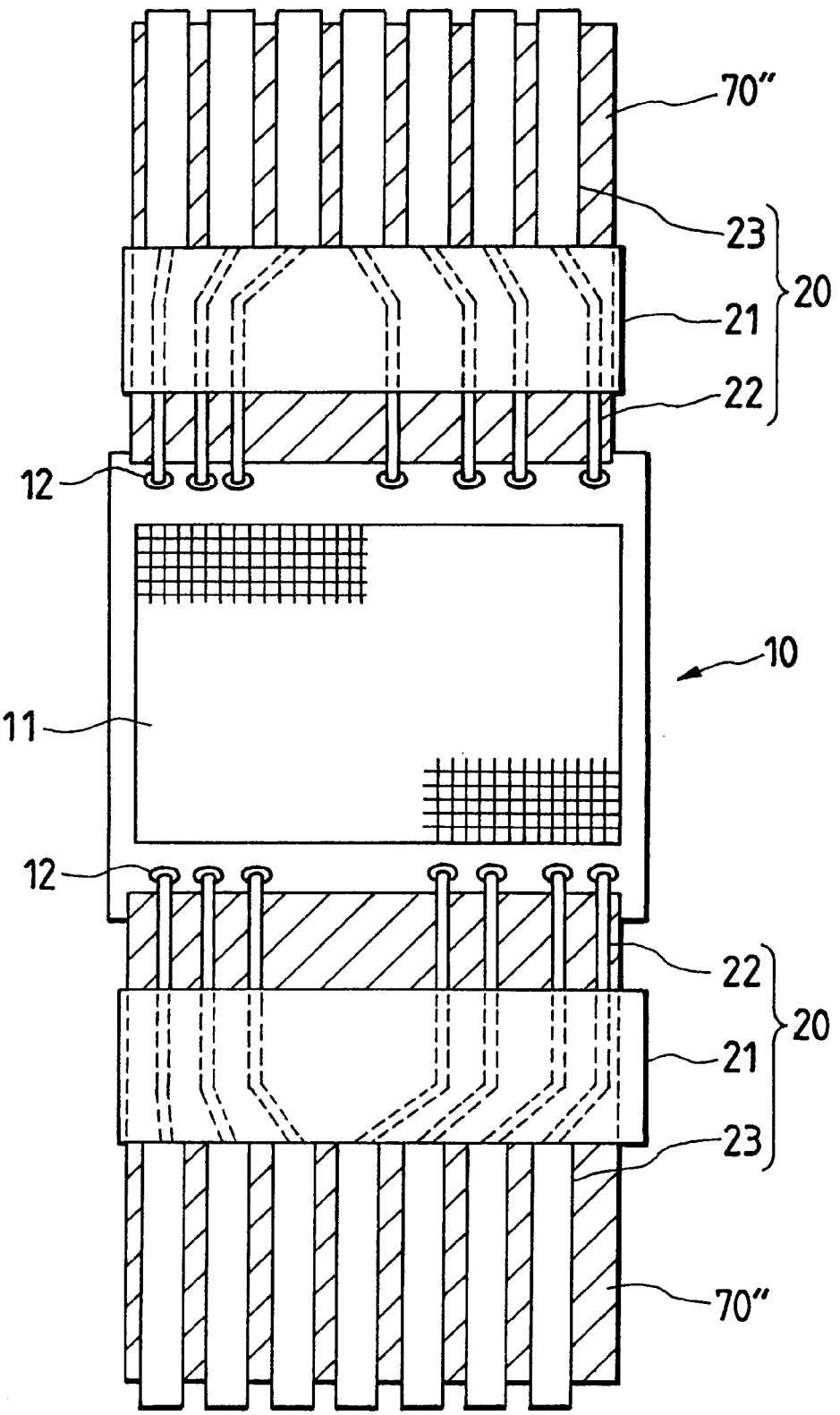
FIG. 12 is a front view of a condition of another unit comprised of a solid-state imaging element and a flexible circuit board before inner leads are bent.

FIG. 12 shows another unit comprised of the solid-state imaging element 10 and the flexible circuit board 20 in which, instead of applying the electrical insulating material 70', sheet-like electrical insulating material 70" is laminated onto the rear surfaces of the inner leads 22 and the leads 23. Polyester, polyimide, etc. can be used as the material for the electrical insulating material 70" and the thickness of the electrical insulating material 70" is in the range of 0.01 mm to 0.1 mm.

The electrical insulating material 70" laminated to the rear surfaces of the inner leads 22 will be sandwiched between the side face of the solid-state imaging element 10 and the inner leads 22 to insulate these members from each other when inner leads 22 are bent as shown in FIG. 9.

As a result, the external dimension L after assembly of the unit comprised of the solid-state imaging element 10 and the flexible circuit board 20 upon bending of the inner leads 22 will be small and the diameter of the front end body 31 can thus be made small to provide excellent insertion properties that will not inflict much pain to a patient.

Figure 14:
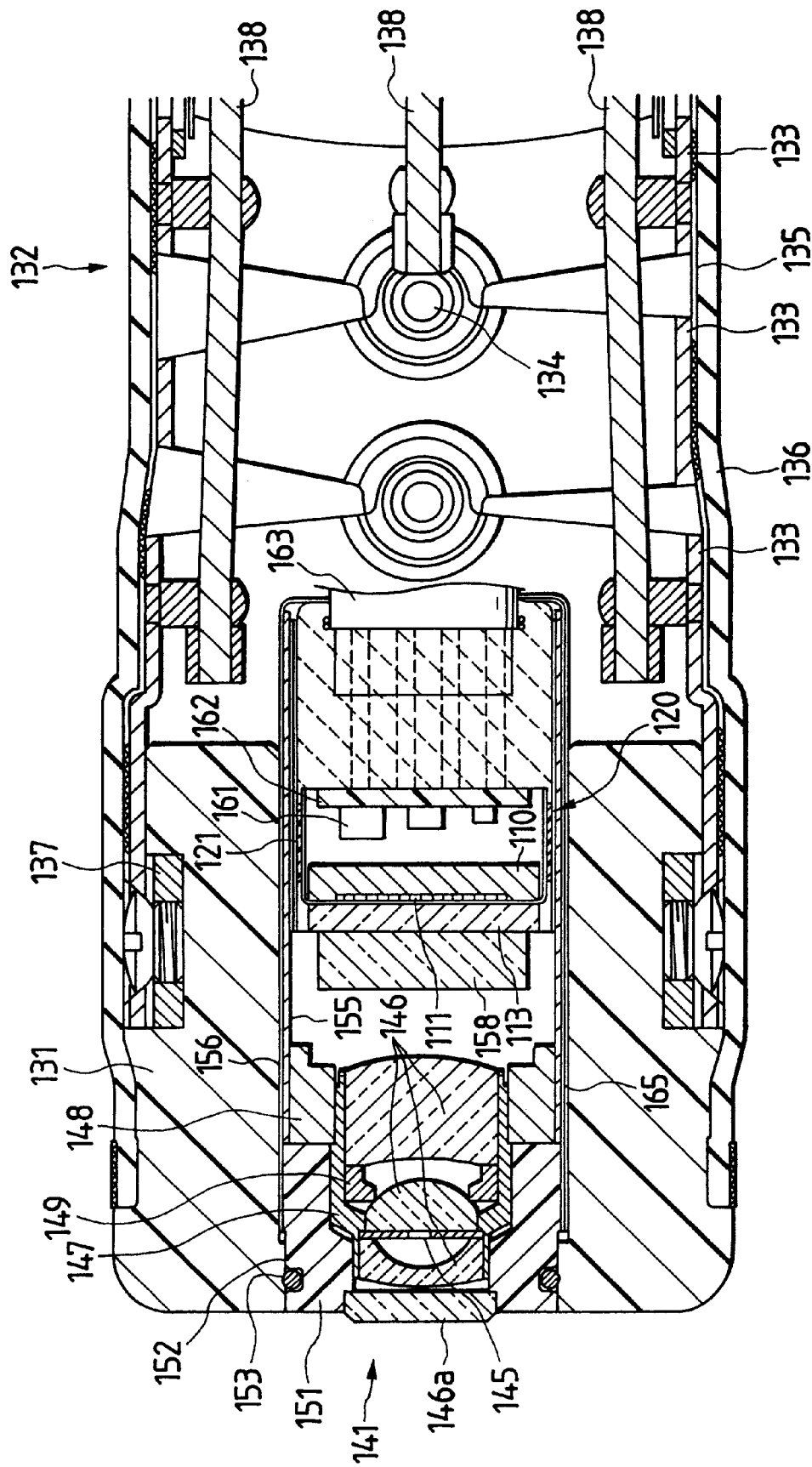
FIG. 14 is a cross-sectional side view of a front end part of the electronic endoscope shown in FIG. 13.

FIG. 14 shows a front end portion of an inserted part of another endoscope.

A front end body 131 is formed from an electrically insulating plastic material and is connected to the front end portion of a bendable part 132, that is disposed at the front end of a thin flexible inserted part and remote-controlled so as to be bent as desired.

The bendable part 132 includes a plurality of joint rings 133 rotatably connected to one another by means of rivets 134, a net tube 135 covering the outer periphery of the joint rings 133, and a jacket 136, made from a rubber tube, etc., covering the outer surface of the net tube 135. The front end part of the jacket 136 is tightly bound and joined to the outer peripheral surface of the front end body 131. Reference numeral 138 is a manipulating wire for controlling degree of bend.

The front end body 131 and the bendable part 132 are connected together such that the forefront joint ring 133 is screwed to a pair of metal threaded pieces 137, each having a female thread and being embedded in a dented part of the front end body 131.

The endoscope is a so-called front view type endoscope arranged for observation in the forward direction, and an observation window 141 is provided on the front end face of the front end body 131. An objective lens group 146 and a solid-state imaging element 110 are disposed inwardly of the observation window 141. These two members are preliminarily assembled as a single unit that is separate from the front end body 131 as shown in an enlarged manner in FIG. 15.

The objective lens group 146 is fixed inside a metal lens frame 147 with a prescribed interval being set between the lenses by means of a spacer 149. Reference numeral 145 is an aperture stop. An insulating ring 151, made of electrically insulating plastic material, is adhered onto the outer peripheral portion of the front half of the lens frame 147.

A cover glass 146a, comprised of a transparent, rectangular parallelpiped plate that is a first optical member of the objective lens group 146, is fitted and adhered in a watertight manner onto the front end face portion (observation window 141 portion) of the insulating ring 151. The side faces of the respective optical members of the objective lens group 146, including the cover glass 146a are finished to a rough surface, and a black-color, antireflection treatment is applied thereto. The character A indicates the light path of the outermost effective ray.

The outer peripheral surface of the insulating ring 151 is formed to have a shape that can be fitted into a hole 152 of a circular cross section that is formed parallel to the axial direction at the front end portion of the front end body 131, and an O-ring 153 for seal is fitted thereto.

A connection member 148, which has an oblong, rectangular external shape, is fixed to the rear end portion of the lens frame 147, and the front end portion of a metal shield pipe 155 is fitted and joined to the outer peripheral part of this connecting member 148.

The shield pipe 155 is formed to have a cylindrical shape with an oblong, rectangular cross section that matches the shape of the solid-state imaging element 110, and is fitted inside a rectangular hole 156 that is made continuous with the circular hole 152 and passes through to the rear end of front end body 131.

A solid-state imaging element 110 for capturing the endoscopic observation image formed by the objective lens group 146 is fixed inside the shield pipe 155 so that the light receiving surface 11 thereof is directed forwardly. The solid-state imaging element 110 is comprised, for example, of a charge coupled device (CCD).

Figure 16:
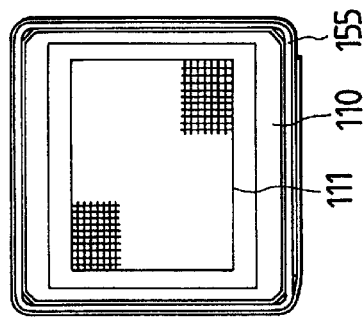
FIG. 16 is a front view of a light receiving surface part of the solid-state imaging element.

As shown in FIG. 16, the light receiving surface 111 of the solid-state imaging element 110 has an oblong, rectangular shape and is positioned at a position at which the subject image is formed by the objective lens group 146. A YAG laser light cut-off filter 158 is adhered onto the front face of the cover glass 113 which in turn is adhered onto the front face of the light receiving surface 111.

Inside the shield pipe 155, electronic parts 161 for processing the signals input to and output from the solid-state imaging element 110 are mounted on a wiring circuit board 162 and disposed behind the solid-state imaging element 110. A signal cable 163 is drawn rearwardly from these electronic parts 161.

Insulating tapes 164 and 165 are respectively wound around the outer peripheral surfaces of the parts disposed inside the shield pipe 155 and the outer peripheral surface of the shield pipe 155 to electrically insulate the shield pipe 155 from inner and outer parts.

A TAB (tape automated bonding) type flexible circuit board 120 is attached to the solid-state imaging element 110, and leads 123 of this flexible circuit board 120 are bent inwards at their rear end portions for connection to the wiring circuit board 162. Reference numeral 121 is a reinforcing plate for the flexible circuit board 120, and it is formed from a thin, electrically insulating plate and is disposed between the flexible circuit board 120 and the inner peripheral face of the shield pipe 155. For electrical insulation between inner leads of the flexible circuit board 120 and the side face of the solid-state imaging element 110, a structure explained with reference to FIGS. 1 to 5 is applied.

Figure 15:
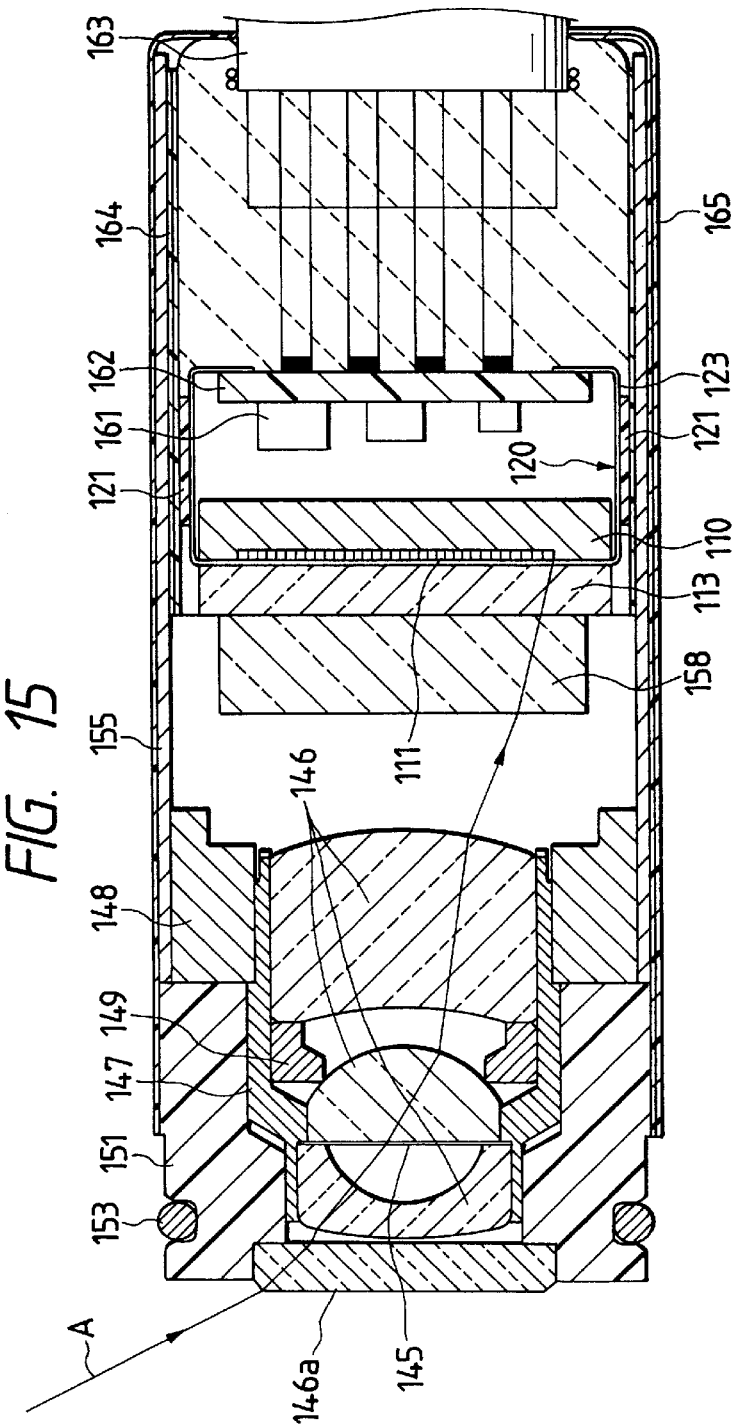
FIG. 15 is an enlarged cross-sectional side view of another unit into which an objective optical group and a solid-state imaging element are assembled.

The unit shown in FIG. 15, in which the objective lens group 146, including the cover glass 146a, the solid-state imaging element 110, etc., are assembled in the manner described above, is inserted from the rear (in other words, from the bendable part 132 side) into the holes 156 and 152 formed through the front end body 131, and is fixed to the front end body 131 by means of an unillustrated fixing screw as shown in FIG. 14.

Since the entire objective lens group 146, including the cover glass 146a, is assembled as a unit beforehand and then installed in the front end body 131, the problem of falling of debris onto the rear face of the cover glass 146a, etc., will not occur in the process of installing the objective lens group 146 in the front end body 131.

And when disassembly, repair, etc., must be performed, the fixing screw can be loosened and the insulating ring 151 can be pushed from the front end side to the inner side to draw out the unit in the direction of the inner side of the front end body 131. The objective lens group 146 can thus be taken out without having to pull the signal cable 163, etc., rearwardly, and disassembly, repair, etc., an be performed readily.

Figure 13:
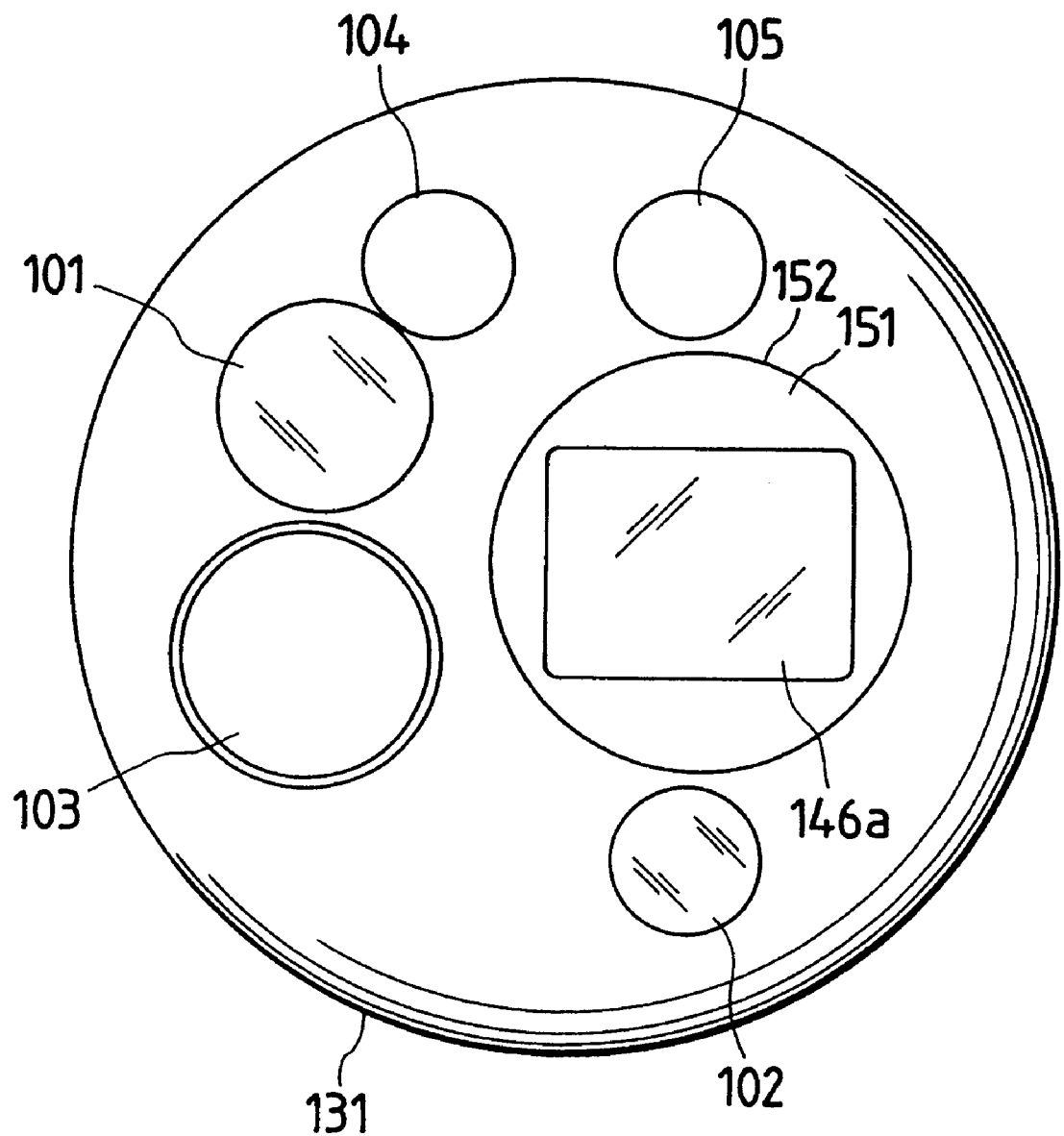
FIG. 13 is a front view of a front end part of another electronic endoscope.

FIG. 13 is a front view of the front end face of the inserted part (that is, the front end view of front end body 131). Reference numerals 101 and 102 are illuminating windows into which concave lenses are fitted, and the exit end face of an illumination light guide is disposed inwardly of each of these windows. Reference numeral 103 is a forceps channel exit, and 104 and 105 are an air delivery nozzle and a water delivery nozzle.

The cover glass 146a, which is mounted to the front end face portion of the insulating ring 151, is formed to have an oblong, rectangular shape that is similar (similar-figure) to the light receiving surface 111 of the solid-state imaging element 110 and that has such a size as to permit all the necessary light rays of the objective lens group 146 to pass but prevent unwanted marginal rays from passing through. Thus, the outermost effective ray A, shown in FIG. 15, passes through a position along and just to the inner side of the edge part of the cover glass 146a.

Unwanted marginal rays are thus completely prevented from entering the objective lens group 146, and satisfactory picture quality without flare, etc., can be obtained without attaching a shading mask, etc., to the objective lens group 146. That is, the entry of unwanted marginal rays into the objective optical system or group 146 can be positively prevented without having to use a shading mask, etc., or without providing a protruded portion that hinders the ease of washing of the surface of the cover glass or first optical member 146a.

Figure 17:
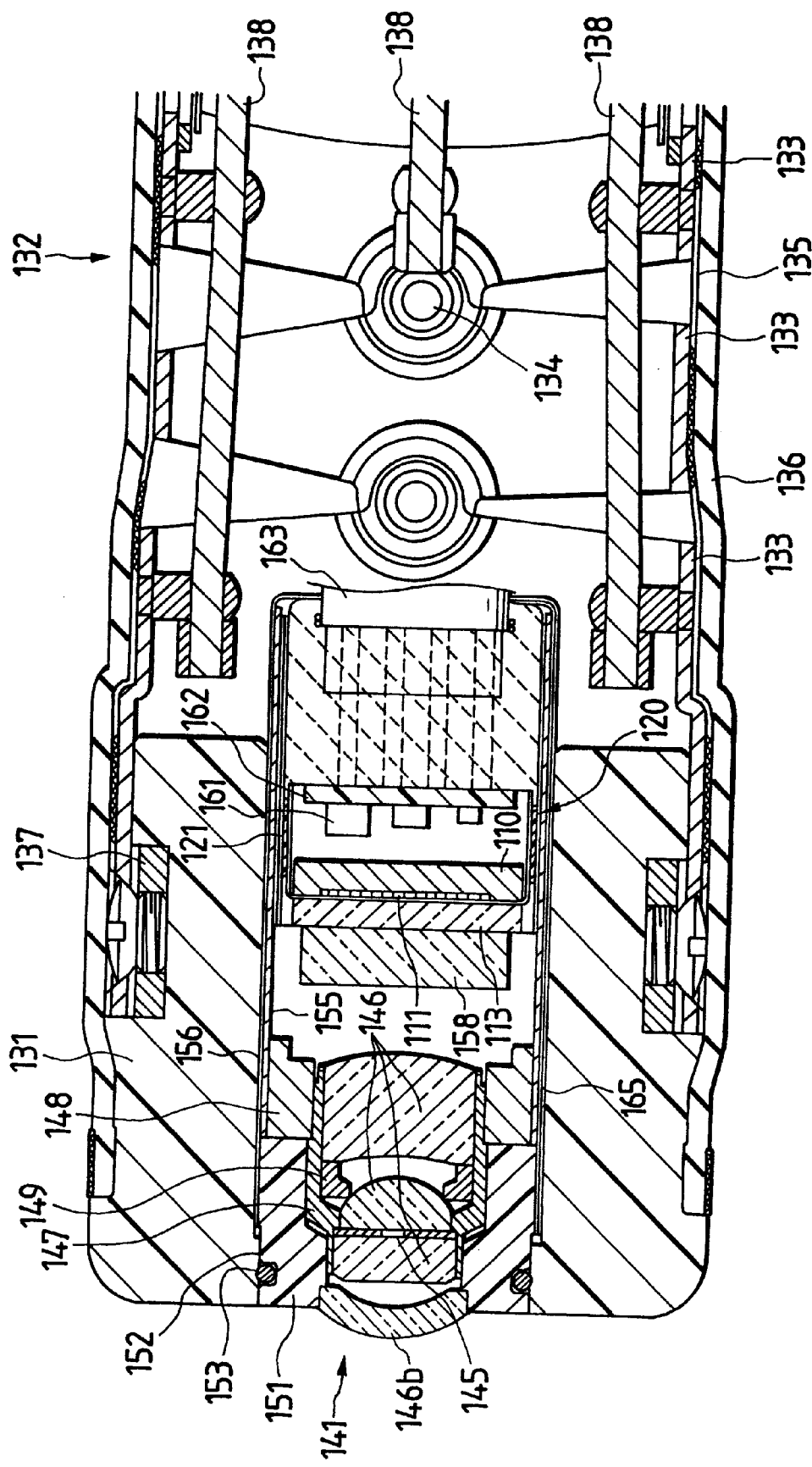
FIG. 17 is a cross-sectional side view of a front end part of another electronic endoscope.

In place of the cover glass 146a, a convex lens 146b, etc., can be used as the first optical member of the objective lens group 46 as shown in FIG. 17, and this convex lens can be an aspherical lens or a meniscus lens.

What is claimed is:

1. A structure for an electronic endoscope, comprising:
    a solid-state imaging element including:
        a light receiving surface;
        pad parts on a portion adjacent said light receiving surface;
        a side face defining an edge at a junction between said portion and said side face;
    a flexible circuit board having inner leads connected to said pad parts, said inner leads being bent to extend along said side face in a rearward direction and being further bent into generally L-shaped portions to extend towards each other and rearwardly of said flexible circuit board, said L-shaped portions defining a space between said inner leads;
    an electrically insulating thin material provided between said side face and said inner leads, said electrically insulating thin material extending from said edge along said side face in said rearward direction, said electrically insulating thin material being attached to said side face; and
    a wiring circuit board positioned to extend substantially parallel to said light receiving surface and within the space defined by said L-shaped portions electrical components being mounted to a first surface of said wiring circuit board that faces into said space, said inner leads and lead wires being connected to a surface of said wiring circuit board opposite said first surface.

2. A structure according to claim 1, wherein said electrically insulating thin material comprises an electrically insulating tape attached to said side face.

3. A structure according to claim 2, wherein said tape has a thickness of 0.01 mm to 0.1 mm.

4. A structure according to claim 3, wherein said tape extends beyond a rear end of said side face in said rearward direction.

5. A structure according to claim 3, wherein said tape is one of polyester and polyimide.

6. A structure according to claim 1, wherein said electrically insulating thin material includes a plurality of electrically insulating tape attached to areas of said side face where said inner leads lie.

7. A structure according to claim 6, wherein each of said tapes has a thickness of 0.01 mm to 0.1 mm.

8. A structure according to claim 7, wherein each of said tapes extends beyond a rear end of said side face in said rearward direction.

9. A structure according to claim 7, wherein each of said tape is one of polyester and polyimide.

10. A structure according to claim 1, further comprising:
    a reinforcing plate attached to said inner leads, wherein said inner leads are located between said reinforcing plate and said electrically insulating thin material.

11. A structure according to claim 1, wherein said electrically insulating thin material includes a reinforcing plate attached to said inner leads.

12. A structure according to claim 11, wherein said reinforcing plate extends beyond a rear end of said side face in said rearward direction.

13. A structure according to claim 12, wherein said reinforcing plate is made of polyimide resin.

14. A structure according to claim 1, wherein said electrically insulating thin material includes coating applied to said inner leads.

15. A structure according to claim 14, wherein said coating has a thickness of 0.01 mm to 0.1 mm.

16. A structure according to claim 15, wherein said coating includes silicone adhesive agent.

17. A structure according to claim 1, wherein said electrically insulating thin material includes a sheet laminated on said inner leads.

18. A structure according to claim 17, wherein said sheet has a thickness of 0.01 to 0.1 mm.

19. A structure according to claim 18, wherein said sheet is one of polyester and polyimide.

20. A structure according to claim 1, wherein said insulating thin material define a substantially constant distance between said side face and said inner leads.

21. A structure according to claim 20, wherein said constant distance is 0.1 mm to 0.01 mm.

22. A structure according to claim 1, wherein said insulating thin material extends from said edge at least to a rear end of said side face in said rearward direction.

23. A structure according to claim 1, wherein said insulating thin material extends from said edge to said pad parts along said portion.

24. A structure for an electronic endoscope, comprising:
    a solid-state imaging element including:
        a light receiving surface;
        pad parts on a portion adjacent said light receiving surface;
        a side face defining an edge at a junction between said portion and said side face;
    a flexible circuit board having inner leads connected to said pad parts, said inner leads being bent to extend along said side face in a rearward direction and being further bent into generally L-shaped portions to extend towards each other and rearwardly of said flexible circuit board, said L-shaped portions defining a space between said inner leads;
    a reinforcing plate attached to said inner leads for reinforcing said inner leads, said reinforcing plate being provided between said side face and said inner leads; and
    a wiring circuit board extending substantially parallel to said light receiving surface, said flexible circuit board further including leads connected to said wiring circuit board and extending with the space defined by said L-shaped portions, electrical components being mounted to a first surface of said wiring circuit board that faces into said space, said inner leads and said lead being connected to a surface of said wiring circuit board opposite said first surface.

25. A structure according to claim 24, wherein said reinforcing plate is electrically insulative.

\* \* \* \* \*

UNITED STATES PATENT AND TRADEMARK OFFICE
CERTIFICATE OF CORRECTION

PATENT NO. : 6,142,930
DATED : November 7, 2000
INVENTOR(S) : K. Ito et al.

Page 1 of 1

It is certified that error appears in the above-identified patent and that said Letters Patent is hereby corrected as shown below:

Title page,
Item [75], Inventors, delete "Hirohisa Ueda".
Item [56], References Cited, FOREIGN PATENT DOCUMENTS, the following references were omitted and should be included:
-- 1-131511    5/1989      Japan
5-323227       12/1993     Japan
7-204159       8/1995      Japan
6-269405       9/1994      Japan
10-211165      8/1998      Japan --
Item [56], References Cited, OTHER PUBLICATIONS, the following references were omitted and should be included:
-- English Language Abstract of JP-5-323227
English Language Abstract of JP-7-204159
English Language Abstract of JP-6-269405
English Language Abstract of JP-10-211165 --
Item [57], ABSTRACT, last line, after "disposed." insert the following new sentences:
-- The inner leads are further bent proximally of the flexible circuit board into generally L-shaped portions to extend towards each other while maintaining a space therebetween. A wiring circuit board disposed substantially parallel to the solid-state imaging element occupies this space and is connected to the inner leads on the proximal surface of the wiring circuit board. --

Signed and Sealed this

Twentieth Day of November, 2001

*Attest:*

*Attesting Officer*

NICHOLAS P. GODICI
*Acting Director of the United States Patent and Trademark Office*